United States Patent [19]

Hasson

[11] Patent Number: 4,744,363
[45] Date of Patent: May 17, 1988

[54] INTRA-ABDOMINAL ORGAN STABILIZER, RETRACTOR AND TISSUE MANIPULATOR

[76] Inventor: Harrith M. Hasson, 2043 N. Sedgwick, Chicago, Ill. 60614

[21] Appl. No.: 882,416

[22] Filed: Jul. 7, 1986

[51] Int. Cl.⁴ .............................................. A61B 17/28
[52] U.S. Cl. .................................. 128/321; 128/303 R
[58] Field of Search ...................... 128/303 R, 327, 20, 128/325, 328, 348.1, 321

[56] References Cited

U.S. PATENT DOCUMENTS

| | | | |
|---|---|---|---|
| 3,411,505 | 11/1968 | Nobis | 128/325 |
| 3,472,230 | 10/1969 | Fogarty | 128/345 X |
| 3,989,049 | 11/1976 | Yoon | 128/325 X |

*Primary Examiner*—Michael H. Thaler
*Attorney, Agent, or Firm*—Wood, Dalton, Phillips, Mason & Rowe

[57] ABSTRACT

An intra-abdominal organ stabilizer, manipulator and retractor includes an elongated tube for insertion through an introducer into an abdominal cavity. A rod is telescopingly received and axially movable within the tube. A stabilizer tip is secured to the distal end of the rod and axially movable therewith into and out of the distal end of the tube. The stabilizer tip includes a pair of relatively stiff juxtaposed support arms laterally flexible between closed positions for movement into and out of the tube, and spread positions when projecting partially or fully beyond the end of the tube for retracting, manipulating or stabilizing organs, tissue or the like during a medical procedure. A leaf spring may be disposed between the support arms for providing rigid horizontal support between the support arms to facilitate manipulation and stabilization of organs or the like and for moving the support arms to their spread positions automatically in response to moving the arms to their extended positions beyond the distal end of the tube. A sleeve or membrane encircles the stabilizer tip and is, in one embodiment, retracted into the tube along with the stabilizer tip. The sleeve when the stabilizer tip is extended bridges the space between the support arms to support the organ or tissue and prevents the organ or tissue from being pinched between the support arms as the stabilizer tip is withdrawn. In another form of the invention, the membrane or sleeve encircles the stabilizer tip and the tube so that when the stabilizer tip is partially or fully extended the end portion of the membrane or sleeve bridges the space between the fully or partially spread apart arms.

20 Claims, 1 Drawing Sheet

U.S. Patent    May 17, 1988    4,744,363
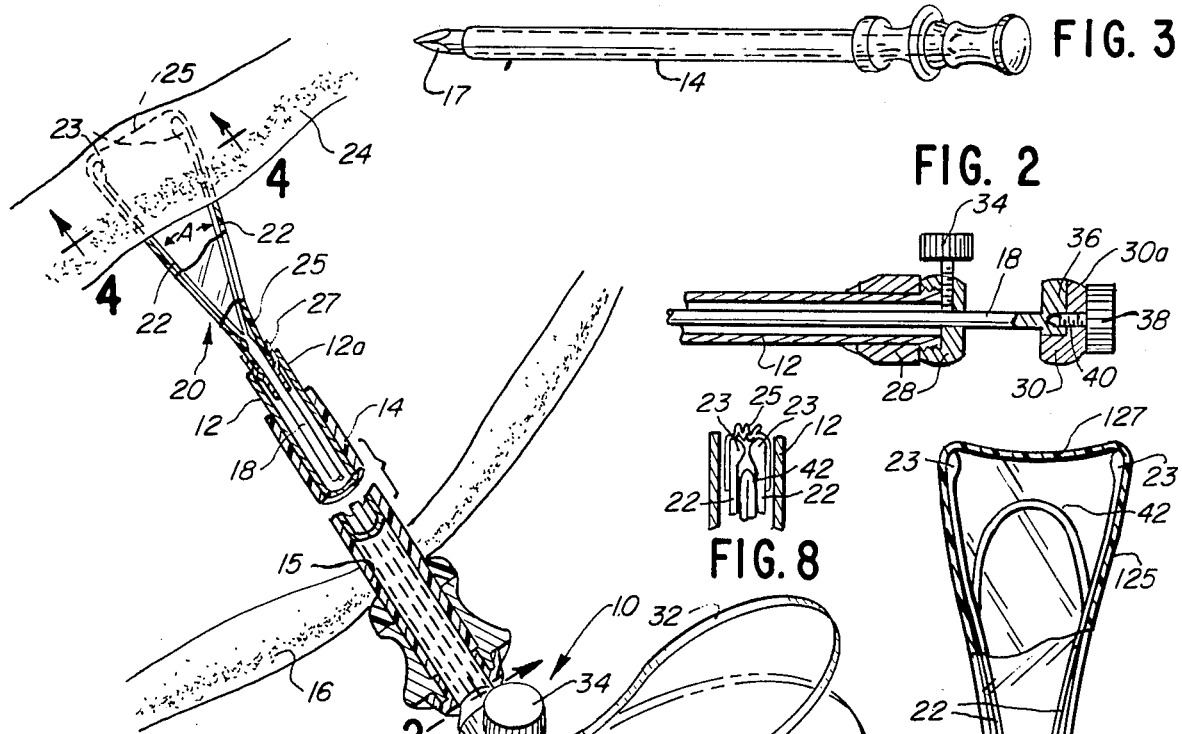
FIG. 3
FIG. 2
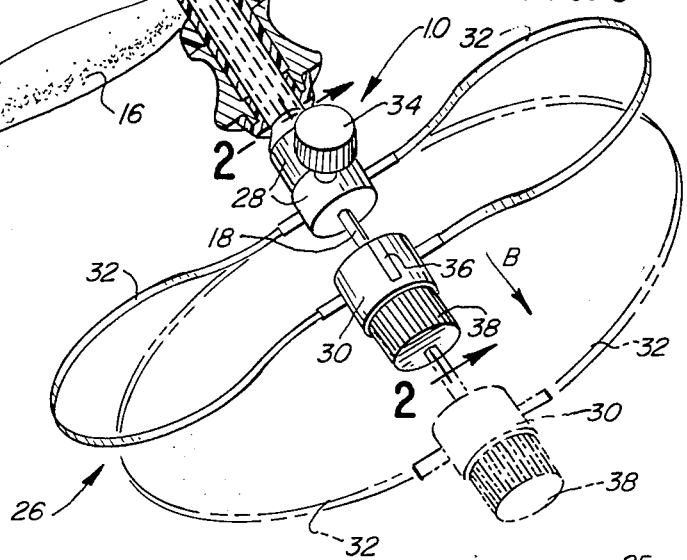
FIG. 1
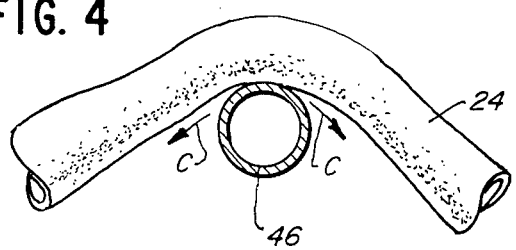
FIG. 4 PRIOR ART
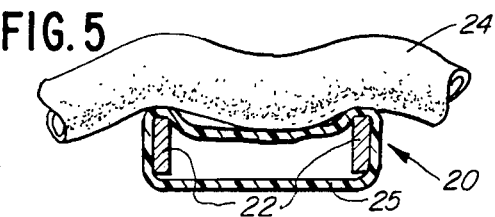
FIG. 5
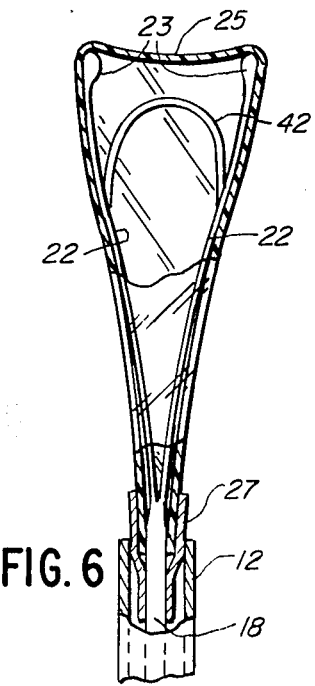
FIG. 6
FIG. 7
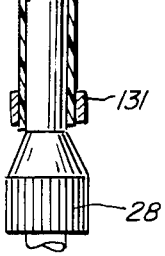
FIG. 8

4,744,363

INTRA-ABDOMINAL ORGAN STABILIZER, RETRACTOR AND TISSUE MANIPULATOR

FIELD OF THE INVENTION

This invention relates to a medical appliance or implement and, more particularly, to an organ stabilizer, tissue manipulator or retractor particularly for use through an aperture or opening in a patient's abdomen or the like.

BACKGROUND OF THE INVENTION

Various medical procedures, such as intra-abdominal operations or diagnoses using a laparoscope, have become increasingly frequent practices. Laparoscopic examinations are conducted for operations or diagnostic work on a patient's pelvic or abdominal organs and tissues. The laparoscope normally is inserted through an aperture in the patient's abdomen near or through the navel.

During the aforesaid operations or examinations, implements must be used to manipulate, stabilize or retract various abdominal organs and tissues during the prescribed procedure. Heretofore, simple rods or elongated probes have been used. However, since many organs such as the ovary, intestines and omentum are extremely slippery, flexible and even "jelly-like", simple rods or probes often have proven ineffective.

This invention is directed to providing a solution to such retracting, manipulative and/or stabilizing problems by providing a new and improved intra-abdominal organ stabilizer, tissue manipulator and retractor.

SUMMARY OF THE INVENTION

An object, therefore, of the invention is to provide a new and improved organ stabilizer of the character described.

In the exemplary embodiment of the invention, an intra-abdominal organ stabilizer/retractor is shown to include an elongated tube for insertion through an introducer sleeve in an aperture or opening in the abdomen. A rod is telescopingly received and axially movable within the tube. A stabilizer tip is secured to the distal or outer end of the rod and is axially movable therewith into and out of the distal end of the tube. The stabilizer tip includes a pair of relatively stiff, juxtaposed support arms laterally flexible between closed positions for movement into and out of the tube, and spread positions when projecting beyond the end of the tube for supporting, stabilizing, manipulating and retracting organs, tissue or the like during a medical procedure. Manipulative means are provided on the proximal end of the tube and operatively associated with the rod for axially moving the rod and the stabilizer tip.

The support arms are generally flat in substantially parallel planes to provide stiffness for support in said planes and to provide flexibility for spreading movement normal to the planes. An inverted U-shaped leaf spring may be secured to the inside of the support arms for automatically moving the arms to their spread positions in response to moving the stabilizer tip axially beyond the distal end of the tube. A thin plastic (such as, latex, rubber or silastic) or fabric (such as, teflon or cloth) membrane, sock or sleeve shaped in the general form of a trapezoid to fit the maximum spreading position of the support arms, covers the support arms and is fastened or molded onto the stabilizer tip. The membrane or sleeve produces a flexible web between the support arms to increase the surface area of the support and manipulation assembly and to prevent tissues from being trapped inside the support arm assembly. The membrane or sleeve is used with or without the inverted U-shaped leaf spring. In another embodiment, the thin plastic (such as, latex, rubber or silastic) or fabric (such as, teflon or cloth) membrane, sock or sleeve is mounted along the exterior of the tube part of the instrument and is fastened to the proximal or inner end portion at the manipulative means.

The manipulative means include means for biasing the rod into a retracted position relative to the elongated tube and, thereby, biasing the stabilizer tip into the tube. The manipulative means also include means for locking the rod and, thereby, the stabilizer tip in any degree of extended, stabilizing position. The manipulative means further include means for preventing rotation of the stabilizer tip relative to the elongated tube.

Other objects, features and advantages of the invention will be apparent from the following detailed description taken in connection with the accompanying drawings.

DESCRIPTION OF THE DRAWINGS

The features of this invention which are believed to be novel are set forth with particularity in the appended claims. The invention, together with its objects and the advantages thereof, may be best understood by reference to the following description taken in conjunction with the accompanying drawings, in which like reference numerals identify like elements in the figures and in which:

FIG. 1 is a fragmented perspective view of the intra-abdominal organ stabilizer/tissue retractor of this invention inserted through a sleeve inserted through an aperture in an abdomen for supporting or retracting an abdominal organ;

FIG. 2 is a fragmented, axial section taken generally along line 2—2 of FIG. 1;

FIG. 3 is a perspective view of a trocar and introducer sleeve for use in placing the intra-abdominal organ stabilizer;

FIG. 4 is a cross-section through a conventional rod-like stabilizer of the prior art;

FIG. 5 is a view similar to that of FIG. 3, but taken generally along line 4—4 of FIG. 1 illustrating the stabilizer tip of the invention.

FIG. 6 is an enlarged plan view of the distal end portion of the organ stabilizer showing a modified structure and illustrating the relationship between the sleeve, the support arms, the rod and the tube; and FIG. 7 is a modification of my intra-abdominal organ stabilizer; and FIG. 8 is a partial section of the stabilizer tip in the retracted position.

DETAILED DESCRIPTION OF THE PREFERRED EMBODIMENT

Referring to the drawings in greater detail, and first to FIG. 1, the invention contemplates an intra-abdominal organ stabilizer, generally designated 10, which includes an elongated tube 12 for threading through a sleeve 14 or cannula inserted through an opening or aperture 15 in the abdominal wall 16. The aperture or opening 15 which is created by means of incising the skin with a knife followed by insertion of the trocar 17 and cannula 14, as shown in FIG. 3, may be selectively located in the lower abdomen. A rod 18 is telescopingly received and axially movable within tube 12.

A stabilizer tip, generally designated 20, is secured to the distal or outer end of rod 18 and is axially movable therewith into and out of the outer (distal) end 12a of tube 12. Stabilizer tip 20 includes a pair of relatively stiff, juxtaposed support arms 22 which are laterally flexible in the direction of double-headed arrow "A" from closed positions for movement into and out of tube 12 when movable thereinto by axial movement of rod 18 in the direction of arrow "B". As seen in FIG. 1, stabilizer support arms 22 are movable to spread positions when projecting beyond the distal end 12a of tube 12 for retracting, supporting, stabilizing or manipulating organs 24, tissues or the like during a medical procedure. The distal ends of support arms 22 are smooth and rounded, as at 23, to provide a rounded, blunt atraumatic distal end for stabilizer tip 20 when the instrument is manipulated inside the abdominal cavity to retract or manipulate various organs and tissues in any degree of extended, stabilizing position or when the instrument is used as an organ stabilizer or tissue retractor/manipulator.

A thin plastic (such as, rubber or silastic) or fabric (such as, teflon or cloth) membrane, sock or sleeve 25 shaped in the general form of a trapezoid to fit the maximum spreading position of the support arms 22, covers the support arms 22 and is fastened onto the stabilizer tip by any appropriate means including molding. One preferred form of fastening the sock to the rod 18 is by means of a retaining collar 27 bridging between the rod 18 and the neck of the membrane or sleeve 25. The membrane or sleeve 25 produces a flexible web between the support arms 22 to increase the surface area of the support and manipulation assembly and to prevent tissues from being trapped inside the support arm assembly. The membrane or sleeve is used with or without an inverted U-shaped leaf spring 42 as shown in FIGS. 6, 7 and 8 and as will be described hereinafter. The collar 27 is secured to the rod 18, overlaps the end of the membrane or sleeve 25 and is secured to the neck of the membrane or sleeve 25. Under one embodiment, the proximal end of the collar 27 will remain in the distal end of the tube 12 thereby reducing the possibility of stripping the sleeve from the support arms 22 during retracting the support arms 22. The membrane or sleeve may be molded onto the support arms and forms an integral function with the rod 18. The membrane 25 is preferred to be very thin so that in its collapsed condition it will not interfere with the withdrawal of the support arms 22 into the tube 12.

Manipulative means, generally designated 26, is provided on the inner or proximal end of tube 12 and is operatively connected with rod 18 for axially moving the rod and stabilizer tip 20 relative to the tube 12. More particularly, and referring to FIG. 2 along with FIG. 1, enlarged bosses 28 are rigidly secured to the inner proximal end of tube 12. A head 30 is rigidly secured to the proximal end of rod 18. Enlarged, U-shaped spring steel bands 32 each are secured at respective opposite ends to boss 28 on tube 12 and head 30 on rod 18. The spring bands bias the head 30 of rod 18 away from bosses 28 of tube 12 as indicated in phantom in FIG. 1 and, thereby, bias stabilizer tip 20, membrane 25 and support arms 22 into the outer distal end 12a of tube 12. In other words, when the rod is in an rearwardly extended position as shown in phantom in FIG. 1, as biased thereto by spring bands 32, support arms 22 are biased together by the periphery of the distal end 12a of tube 12 whereby the support arms and membrane are retracted into the tube to permit the tube to be inserted through the introducer sleeve 14. Once inserted to a proper position, as might be visualized through a laparoscope, the head 30 of rod 18 is pushed in a telescoping manner within tube 12, compressing spring bands 32, so that the stabilizer tip 20 is moved beyond the distal end 12a of tube 12 whereby support arms 22 can expand and spread the membrane 25 apart for use in stabilizing an organ, retracting tissue or the like.

Manipulative means 26 include means for locking rod 18 and, thereby, stabilizer tip 20 in an extended position as shown in full lines in FIG. 1. More particularly, a set screw 34 is threaded through boss 28 as seen in FIG. 2 to clamp onto the outer periphery of rod 18 and lock the rod in any axial position relative to tube 12.

Manipulative means 26 further include means to prevent rotation of rod 18 and, thereby, stabilizer tip 20 relative to tube 12. More particularly, as seen in FIGS. 1 and 2, an upwardly projecting key 36 on rod 18 is received within a complementary keyway in head 30 which head 30 slides longitudinally on the outer end of rod 18. Since head 30 is prevented from rotation relative to tube 12 by means of band springs 32, rod 18 cannot rotate angularly relative to tube 12. Head 30, which is secured to band springs 32 is secured to the outer end of rod 18 by means of a small thumb bolt 38 which sandwiches a portion 30a of head 30 between key 36 and thumb bolt 38. The bolt is threaded into a threaded bore 40 in the proximal end of rod 18.

Referring to the modification shown in FIGS. 6, 7 and 8 another structure is provided for positively spreading the support arms 22 and for aiding in the supporting, manipulating and/or retracting operations. That is, an inverted U-shaped leaf spring 42 is attached to the support arms 22 between the support arms 22. The leaf spring 42 provides a rigid horizontal means of support for the sleeve or membrane 25 between the support arms to render the support and manipulation assembly more rigid in general. The leaf spring also provides a firm support for the membrane or sleeve 25 when the support arms are only partially extended. That is, with the support arms only partially extended, the membrane or sleeve is not fully pulled between the support arms and could sag between the support arms and therefore not provide the desired support for retracting or manipulating the tissue. With the leaf spring between the support arms, the membrane or sleeve is supported by the leaf spring whether or not the support arms are partially or fully extended. Many procedures require retracting or manipulating tissue before the ultimate tissue support function is performed. The retracting or manipulating is performed more often than not with the support arms only partially extended. It is during this stage of the procedure that the leaf spring support of the sleeve or membrane 25 is important.

Specifically, the leaf spring 42 aids in moving the support arms 22 to their spread positions automatically in response to moving the arms, with rod 18, to the extended position beyond the distal end of tube 12. It can be seen in FIG. 6 that the "U" shape of the spring is directed proximally. The leaf spring, along with spring bands 32, may be fabricated of spring steel-type material. Therefore, as the support arms and membrane or sleeve 25 are withdrawn within tube 12, leaf spring 42 simply collapses. As stabilizer tip 20 is moved axially to its extended position, leaf spring 42 automatically spreads support arms 22 and membrane or sleeve 25 to a stabilizing position. The horizontal rigid support means also facilitates manipulating and stabilizing organs 24, tissue or the like.

In order to prevent tissue 24 from becoming lodged or entangled in the crevices between the support arms 22 and/or the leaf spring 42 and support arms 22, particularly during collapsing of stabilizer tip 20, the membrane or sleeve 25 (FIGS. 1, 5 and 6) is located around the support arms 22 and across the legs of U-shaped spring.

FIG. 8 shows the relationship between the support arms 22, rounded tips 23, inverted U-shaped leaf spring 42, membrane 25 and tube 12 when the support arms 22 are withdrawn into the tube 12. The leaf spring 42 collapses into the space provided by the tips 23 abutting each other with the thin membrane 25 up around the support arms 22 inside the tube 12.

FIGS. 4 and 5 show somewhat schematically the difference between prior art stabilizing rods or probes 46 (FIG. 4) and the stabilizer tip 20 (FIG. 5) of the invention. Operations of the type herein involved are usually conducted under laparoscopic vision and control. When using a prior art stabilizing probe 46, tissue 24 has a tendency to simply slide across the probe as indicated by arrows "C" and, often, the tissue will slide off of the end of the probe. It can be seen in FIG. 5 that a considerably larger supporting surface area is provided by stabilizer tip 20 because the tip is in an expanded or spread condition when within the patient's body. Yet, on insertion and withdrawal of stabilizer 10 from its operative position, the stabilizer tip is contracted and withdrawn to a dimension no bigger than probe 46 as defined by tube 12 of the invention. FIG. 5 also shows that support arms 22 actually are generally flat in parallel planes to provide stiffness for support in those planes, generally normal to tissue 24. The thin, flat support arms surrounded by the membrane or sleeve 25 bridging the gap therebetween provide a large and stable support surface for stabilizing or retracting the organ 24 during the conduct of the procedure.

FIG. 7 shows another modified form of the invention. The support arms 22, tube 12, rod 18 and manipulator assembly 26 are the same as described in FIGS. 1 and 6. The U-shaped spring 42 could be eliminated, if desired. A sock or sleeve 125 which may be plastic or a fabric is provided and encases substantially the full length of the tube 12 and stabilizer tip 20. That is, sleeve 125 with an inverted truncated distal end portion 127, and a tubular body portion 129 encases the extended stabilizer tip 20 and tube 12 and is fastened to the tube 12 at the base 28 as by a collar 131. When the stabilizer tip is withdrawn into the tube 12, the sleeve 125 initially recovers its stretch and then is manually pulled or worked back by the operator as the stabilizer tip is withdrawn.

With the stabilizer tip 20 retracted and the sleeve 125 also retracted to encase the distal end of the tube 12, the instrument may be threaded through a cannula 14 into the abdominal cavity. Once inserted to a proper position as visualized through a laparoscope, the stabilizer tip and sleeve 125 are extended, are locked in an extended or partially extended position by tightening screw 34 and the instrument is maneuvered to elevate, retract or stabilize the tissue or organ.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. An intra-abdominal organ stabilizer, manipulator and retractor comprising:
    an elongated tube for insertion through an introducer sleeve into an abdominal area;
    a relatively stiff stabilizer tip at the distal end of the tube, the tip being convertible from a collapsed condition for insertion through the introducer sleeve to an expanded condition for retracting, manipulating, supporting and stabilizing organs, tissue or the like, the stabilizer tip being sized for withdrawal into the tube when in collapsed condition;
    a thin membrane bridging any open space between the expanded condition of the tip for supporting, manipulating, retracting and stabilizing organs, said membrane being withdrawn into the tube along with the stabilizer tip; and
    manipulative means on the proximal end of the tube and operatively associated through the tube with the stabilizer tip for converting the tip between its collapsed and expanded conditions.

2. The stabilizer of claim 1 wherein said stabilizer tip includes a pair of juxtaposed support arms movable between a closed position defining said collapsed condition of the tip and a spread position defining said expanded condition of the tip.

3. The stabilizer of claim 2 wherein said manipulative means include means for moving the support arms axially between withdrawn positions substantially within the tube and extended positions substantially beyond the distal end of the tube permitting movement of the support arms to their spread positions.

4. The stabilizer of claim 3, including means for automatically moving said support arms to their spread positions in response to moving the arms to the extended positions beyond the distal end of the tube.

5. The stabilizer of claim 4 wherein said automatic moving means comprises spring means between the support arms.

6. The stabilizer of claim 5 wherein said spring means comprises an inverted U-shaped leaf spring secured at its opposite ends to the inside of the support arms.

7. The stabilizer of claim 6 wherein said membrane comprises a sleeve means encircling the support arms for preventing tissue from becoming lodged in the crevices therebetween.

8. The stabilizer of claim 7 wherein said sleeve means encircles said tube and is affixed at the proximal end of the tube.

9. The stabilizer of claim 1 wherein said manipulative means include means for locking the stabilizer tip in its expanded condition.

10. The stabilizer of claim 1 wherein said manipulative means include means for preventing rotation of the stabilizer tip relative to said tube.

11. The stabilizer of claim 1 wherein said membrane comprises a sleeve encircling the support arms and being secured to the base of the tip.

12. An intra-abdominal organ stabilizer, retractor and manipulator comprising:
    an elongated tube for insertion through an introducer sleeve into the abdominal cavity;
    a rod telescopingly received and axially movable within the tube;

a stabilizer tip secured to the distal end of the rod and axially movable therewith into and out of the distal end of the tube, the stabilizer tip consisting of a pair of relatively stiff juxtaposed support arms laterally flexible between closed positions for movement into and out of the tube and spread positions when projecting beyond the end of the tube for supporting, retracting, manipulating and stabilizing organs, tissue or the like during a medical procedure, wherein said support arms are generally flat in generally parallel planes to provide stiffness for support in said planes and to provide flexibility for spreading movement normal to the planes;

a membrane secured to the rod and encircling the support arms for bridging between the support arms to further support the organs, tissue, or the like, and manipulative means on the proximal end of the tube and operatively associated with the rod for axially moving the rod, support arms and encircling membrane into and out of the tube.

13. The stabilizer of claim 12 wherein said manipulative means include means for biasing the rod in the proximal direction and, thereby, biasing the stabilizer tip into the tube.

14. The stabilizer of claim 13 wherein said manipulative means include means for locking the rod and, thereby, the stabilizer tip in a partially or fully extended position.

15. The stabilizer of claim 12 wherein said manipulative means include means for preventing rotation of the stabilizer tip relative to said tube.

16. The stabilizer of claim 12 wherein said means for encircling the support arms comprises a membrane closed at the distal end and secured to the rod, and wherein said support arms and membrane are moved into and out of the tube.

17. The stabilizer of claim 12 wherein said means for encircling said stabilizer tip comprises a membrane closed over the end of the tip and secured to the tube at the proximal end of said tube.

18. The stabilizer of claim 12, including means for automatically moving said support arms to their spread positions in response to moving the arms to the extended positions beyond the inner end of the tube.

19. The stabilizer of claim 18 wherein said automatic moving means comprise spring means between the support arms.

20. The stabilizer of claim 19 wherein said spring means comprises an inverted U-shaped leaf spring secured at its opposite ends to the inside of the support arms.

* * * * *